United States Patent
Finkelman et al.

(10) Patent No.: US 9,795,618 B2
(45) Date of Patent: Oct. 24, 2017

(54) METHODS AND COMPOSITIONS FOR SUPPRESSING IGE-MEDIATED ANAPHYLAXIS

(71) Applicant: University of Cincinnati, Cincinnati, OH (US)

(72) Inventors: Fred D. Finkelman, Cincinnati, OH (US); Marat V. Khodoun, Mason, OH (US); Suzanne C. Morris, Mason, OH (US)

(73) Assignee: University of Cincinnati, Cincinnati, OH (US)

( * ) Notice: Subject to any disclaimer, the term of this patent is extended or adjusted under 35 U.S.C. 154(b) by 69 days.

(21) Appl. No.: 14/633,305

(22) Filed: Feb. 27, 2015

(65) Prior Publication Data

US 2015/0246125 A1 Sep. 3, 2015

Related U.S. Application Data

(60) Provisional application No. 61/946,212, filed on Feb. 28, 2014.

(51) Int. Cl.

| | |
|---|---|
| *A61K 31/573* | (2006.01) |
| *A61K 31/4439* | (2006.01) |
| *A61K 31/675* | (2006.01) |
| *A61K 31/506* | (2006.01) |
| *A61K 31/4709* | (2006.01) |
| *A61K 31/137* | (2006.01) |
| *A61K 31/335* | (2006.01) |
| *A61K 45/06* | (2006.01) |
| *C07K 16/42* | (2006.01) |
| *A61K 39/00* | (2006.01) |

(52) U.S. Cl.
CPC .......... *A61K 31/573* (2013.01); *A61K 31/137* (2013.01); *A61K 31/335* (2013.01); *A61K 31/4439* (2013.01); *A61K 31/4709* (2013.01); *A61K 31/506* (2013.01); *A61K 31/675* (2013.01); *A61K 45/06* (2013.01); *C07K 16/4291* (2013.01); *A61K 2039/505* (2013.01)

(58) Field of Classification Search
None
See application file for complete search history.

(56) References Cited

U.S. PATENT DOCUMENTS

| 8,003,127 | B2 | 8/2011 | Liversidge et al. | |
|---|---|---|---|---|
| 2005/0158303 | A1* | 7/2005 | Liu | A61K 9/0019 424/131.1 |
| 2009/0010924 | A1* | 1/2009 | Wu | A01K 67/0278 424/131.1 |
| 2013/0243750 | A1* | 9/2013 | Scheerens | A61K 39/39566 424/131.1 |
| 2014/0314783 | A1 | 10/2014 | Finkelman et al. | |

OTHER PUBLICATIONS

Gaestel et al (Nature Reviews, 8: 480-499, 2009).*
Meglio et al, "A protocol for oral desensitization in children with IgE-mediated cow's milk allergy," European J. of Allergy and Clinical Immunology 59(9): 980-87 (2004).
Khodoun et al, "Rapid polyclonal desensitization with antibodies to IgE and FcεRIa," J. Allergy Clin. Immunol, pp. 1555-1564, Jun. 2013.
Mirkina et al, "Inhibition of human cord blood-derived mast cell responses by anti-FcεRI mAb 15/1 versus anti-IgE Omalizumab," Immunology Letters 109 (2007), pp. 120-128.
Khodoun et al, "Rapid desensitization of mice with anti-FcgRIIb/FcgRIII mAb safely prevents IgG-mediated anaphylaxis," J. Allergy Clin. Immunol., pp. 1375-1387, Dec. 2013.

* cited by examiner

*Primary Examiner* — Lei Yao
(74) *Attorney, Agent, or Firm* — Dinsmore & Shohl LLP (57) ABSTRACT

Methods for suppressing IgE-mediated anaphylaxis are provided herein, which include administering to a person in need thereof a combination of at least two therapeutic agents selected from the group consisting of an antihistamine, one or more beta-adrenergic agonists, and one or more tyrosine kinase antagonists. Also provided herein are methods of suppressing IgE-mediated anaphylaxis associated with immunotherapeutic desensitization of a subject, and pharmaceutical compositions for suppressing IgE-mediated anaphylaxis.

15 Claims, 10 Drawing Sheets

METHODS AND COMPOSITIONS FOR SUPPRESSING IGE-MEDIATED ANAPHYLAXIS

RELATED APPLICATION

This application claims the benefit of U.S. Provisional application Ser. No. 61/946,212, filed Feb. 28, 2014, which application is hereby incorporated by reference in its entirety.

FEDERALLY SPONSORED RESEARCH OR DEVELOPMENT

The presently disclosed technology was developed with United States government support pursuant to Grant No. R01 AI113162-02, awarded by the National Institutes of Health. The United States government may have certain rights therein.

FIELD OF THE INVENTION

The presently disclosed subject matter relates to the field of suppressing anaphylaxis associated with immunotherapeutic desensitization methods. Specifically, the present invention relates to methods and pharmaceutical compositions for suppressing IgE-mediated anaphylaxis comprising administering a combination of therapeutic agents.

BACKGROUND OF THE INVENTION

Immunoglobulin E (IgE) antibody plays a key role in allergic disease. IgE primes the IgE-mediated allergic response by binding to Fc receptors found on the surface of mast cells and basophils. Fc receptors include FcεRI and FcεRII. IgE that can specifically recognize an allergen has a unique, long-lived interaction with its high-affinity receptor FcεRI such that basophils and mast cells become primed and ready to release and/or secrete histamine, leukotrienes, additional vasoactive mediators, proteolytic enzymes, and certain interleukins. The release of these chemicals can cause symptoms associated with allergy, including airway constriction, local inflammation, increased mucous secretion, increased vascular permeability, and anaphylaxis.

Anaphylaxis is an acute and potentially life-threatening hypersensitivity reaction involving the release of mediators from mast cells, basophils, and recruited inflammatory cells. Anaphylaxis is the term given to signs and symptoms that occur after exposure to a provoking agent. These signs and symptoms can develop within minutes or hours of exposure. Anaphylaxis can range from mild to severe in nature. Severe initial symptoms develop rapidly, reaching peak severity within 5 to 120 minutes. Death from shock, asthma, or airway swelling can occur within minutes of onset of anaphylaxis. In some instances, protracted anaphylaxis can occur, with symptoms persisting for days.

Anaphylaxis is mediated by immediate hypersensitivity reactions in which the activation of inflammatory cells by the crosslinking of immunoglobulin (Ig) Fc receptors (R) leads rapidly to the release of vasoactive mediators, such as histamine and platelet activating factor (PAF), cytokines, and proteolytic enzymes. Such immediate hypersensitivity reactions are the critical pathogenic mechanism in anaphylaxis and IgE-mediated food allergy. In both humans and mice, immediate hypersensitivity reactions can be mediated by antigen crosslinking of antigen-specific IgE bound to the high affinity IgE receptor, FcεRI, on mast cells and basophils.

Although some allergic disorders can be treated pharmacologically, immunotherapy offers another therapeutic option. Allergen immunotherapy involves administering increasing doses of allergen to accustom the body to substances that are generally harmless (grass, pollen, dust mites), thereby inducing desensitization, which is usually short term, or tolerance, which can be long-lasting. Although effective, administration of allergen can be of limited utility in individuals who are allergic to multiple antigens. In addition, the presence of serum antibodies, including IgG, which can bind to inoculated allergens, may make rapid desensitization more risky if the initial, small allergen doses are neutralized before they can access mast cell or basophil bound IgE, such that the first dose of allergen that interacts with cell-bound IgE is sufficiently large to induce a severe reaction, which may include anaphylaxis.

Desensitization with antibodies such as anti-FcεRIα monoclonal antibody (mAb) and anti-IgE mAb provides another option for inhibiting IgE-mediated hypersensitivity. See, for example, U.S. Publication No. 2014/0314783, by Finkelman, et al., incorporated herein by reference in its entirety. However, in certain instances, particular dosing regimens of such antibodies can also induce IgE-mediated anaphylaxis.

The need exists to develop compositions and methods for suppressing IgE-mediated anaphylaxis, particularly, but not exclusively, for use in methods of allergen desensitization via administration of antigen or monoclonal antibodies such as anti-IgE and anti-FcεRIα.

SUMMARY OF THE INVENTION

Accordingly, methods and compositions for suppressing IgE-mediated anaphylaxis are provided herein. In one embodiment, a method of suppressing IgE-mediated anaphylaxis is provided, comprising administering to a subject in need thereof a combination of at least two therapeutic agents selected from the group consisting of an antihistamine, one or more beta-adrenergic agonists, and one or more tyrosine kinase antagonists.

In another embodiment, a method of suppressing IgE-mediated anaphylaxis associated with immunotherapeutic desensitization of a subject in need thereof is provided, comprising (a) pretreating the subject with a combination of at least two therapeutic agents selected from the group consisting of an antihistamine, one or more beta-adrenergic agonists, and one or more tyrosine kinase antagonists; and (b) administering to the subject an antibody selected from the group consisting of an anti-IgE monoclonal antibody, an anti-Fc epsilon receptor I alpha (FcεRIα) monoclonal antibody, and combinations thereof, wherein the pretreating step (a) suppresses IgE-mediated anaphylaxis in the subject.

In another embodiment, a pharmaceutical composition for suppressing IgE-mediated anaphylaxis is provided, comprising (a) a safe and effective amount of at least two therapeutic agents selected from the group consisting of triprolidine, doxepin, indacaterol, terbutaline, albuterol, imatinib, and fostamatinib; and (b) one or more pharmaceutically-acceptable excipients.

These and other objects, features, embodiments, and advantages will become apparent to those of ordinary skill in the art from a reading of the following detailed description and the appended claims.

BRIEF DESCRIPTION OF THE DRAWINGS

FIG. 2A shows the vehicle/saline challenge vs. vehicle/anti-IgE antibody EM-95 challenge. FIG. 2B shows each of triprolidine, indacaterol, and fostamatinib in combination with EM-95 challenge. FIG. 2C shows triprolidine+fostamatinib, triprolidine+indacaterol, and indacaterol+fostamatinib, each in combination with EM-95 challenge. FIG. 2D shows triprolidine+indacaterol+fostamatinib in combination with EM-95 challenge. FIGS. 2E and 2F show a comparison of vehicle/saline, vehicle/anti-IgE antibody, and each of triprolidine, indacaterol, fostamatinib, triprolidine+indacaterol, triprolidine+fostamatinib, indacaterol+fostamatinib, and indacaterol+triprolidine+fostamatinib, in combination with anti-IgE antibody challenge. Anaphylaxis/suppression is measured by temperature change over time (FIGS. 2A-2D), and maximum (max) temperature drop (FIG. 2E); mast cell degranulation is measured by serum MMCP1 (FIG. 2F).

DETAILED DESCRIPTION OF THE INVENTION

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, doses, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "subject" refers to any mammalian subject, including mice, rats, rabbits, pigs, non-human primates, and humans.

As used herein, the term "suppressing IgE-mediated anaphylaxis" refers to slowing and/or stopping the progression of the release of vasoactive mediators and/or symptoms associated with anaphylaxis that can be caused by these vasoactive mediators. In certain embodiments, the IgE-mediated anaphylaxis is induced by the administration of antigen or by desensitization methods involving the administration of antigen. In other embodiments, the IgE-mediated anaphylaxis is induced by an anti-IgE monoclonal antibody (mAb) and/or an anti-Fc epsilon receptor I alpha (FcεRIα) monoclonal antibody or by desensitization methods involving the administration of an anti-IgE monoclonal antibody (mAb) and/or an FcεRIα mAb.

The term "treating," as used herein, includes treatment of existing disease and prophylactic treatment of those at risk of developing the disease.

The term "administering," as used herein, refers to any route of administering a safe and effective amount of a therapeutic agent. In some embodiments, the administering includes, but is not limited to, oral, intravenous, subcutaneous, intramuscular, intraperitoneal, sublingual, rectal, nasal, pulmonary, and transdermal administration.

The term "antihistamine," as used herein, refers to a compound that blocks histamines and relieves symptoms of allergy. Suitable antihistamines are listed in U.S. Pat. No. 8,242,110, to Deregnaucourt, et al., incorporated by reference herein in its entirety. In certain embodiments, the antihistamine is suitable for systemic use. In specific embodiments, the antihistamines triprolidine and doxepin are suitable for use in the presently disclosed compositions and methods.

The term "beta-adrenergic agonist," as used herein, refers to a compound that acts on beta adrenoreceptors, relaxing the airway muscles, widening airways, and increasing the frequency and strength of cardiac contractions. Beta-adrenergic agonists mimic the action of epinephrine and norepinephrine signaling in the heart, lungs, and smooth muscle tissue. A variety of beta-adrenergic agonists are known in the art. See, for example, U.S. Pat. No. 8,324,266, to Vehring, et al., incorporated by reference herein in its entirety. In specific embodiments of the presently disclosed compositions and methods, the beta-adrenergic agonist is selected from the group consisting of terbutaline, albuterol, indacaterol, and combinations thereof.

The term "tyrosine kinase antagonist," as used herein, refers to a compound that inhibits tyrosine kinase enzyme activity. A variety of tyrosine kinase antagonists are known in the art, including, but not limited to, bosutinib, crizotinib, dasatinib, erlotinib, imatinib, lapatinib, nilotinib, sorafenib, sunitinib, and fostamatinib, any of which are suitable for use in the present methods and compositions. In specific embodiments, the tyrosine kinase antagonist suitable for use in the presently disclosed compositions and methods is selected from the group consisting of imatinib, fostamatinib, and combinations thereof.

Fostamatinib is an experimental tyrosine kinase antagonist drug candidate for the treatment of a variety of diseases. Fostamatinib is administered orally as a disodium salt, and is a prodrug of the active compound tamatinib (R-406), which is an inhibitor of the enzyme spleen tyrosine kinase (Syk). Fostamatinib was found to be safe but not highly effective in the treatment of rheumatoid arthritis in phase III clinical trials; however, as disclosed herein, fostamatinib has surprisingly been found to synergize with other therapeutic agents to suppress IgE-mediated anaphylaxis in vivo. Further, fostamatinib has surprisingly been found to inhibit mast cell and basophil degranulation in vivo.

The term "immunotherapeutic desensitization," as used herein, refers to desensitization of IgE-mediated allergy through administration of antigen or antibodies. Immunotherapeutic desensitization through the administration of antigen is generally accomplished via monitored administration of increasing doses of antigen. See, for example, Meglio, et al., "A protocol for oral desensitization in children with IgE-mediated cow's milk allergy," *European J. of Allergy and Clinical Immunology* 59(9): 980-87 (2004), incorporated by reference herein in its entirety. Immunotherapeutic desensitization through the administration of antibodies can be accomplished using a variety of antibodies, including but not limited to, anti-FcεRIα mAb, and anti-IgE mAb. See, for example, U.S. Publication No. 2014/0314783, by Finkelman, et al.

Methods of Suppressing IgE-Mediated Anaphylaxis

In one embodiment, a method of suppressing IgE-mediated anaphylaxis is provided, comprising administering to a subject in need thereof a combination of at least two therapeutic agents selected from the group consisting of an antihistamine, one or more beta-adrenergic agonists, and one or more tyrosine kinase antagonists. In some embodiments, the method comprises administering an antihistamine in combination with one or more beta-adrenergic agonists, or an antihistamine in combination with one or more tyrosine kinase antagonists. In other embodiments, the methods comprise administration of two or more beta-adrenergic agonists in combination, or two or more tyrosine kinase antagonists in combination. In still other embodiments, the methods comprise administration of a combination of an antihistamine, at least one beta-adrenergic agonist, and at least one tyrosine kinase antagonist. In another embodiment, the method comprises administering at least two therapeutic agents selected from the group consisting of triprolidine, doxepin, indacaterol, terbutaline, albuterol, imatinib, and fostamatinib.

In other embodiments, the method further comprises the step of desensitizing the subject by administering an antigen or an antibody selected from the group consisting of an anti-IgE monoclonal antibody, an anti-Fc epsilon receptor I alpha (FcεRIα) monoclonal antibody, and combinations thereof. In specific embodiments, the antihistamine is selected from the group consisting of triprolidine, doxepin, and combinations thereof. In certain embodiments, the beta-adrenergic agonist is selected from the group consisting of indacaterol, terbutaline, and albuterol. In certain embodiments, the tyrosine kinase antagonist is selected from the group consisting of imatinib and fostamatinib.

In another embodiment, the method further comprises administering a corticosteroid in addition to the at least two therapeutic agents. A variety of corticosteroids suitable for use in the present compositions and methods are known in the art. See, for example, U.S. Pat. No. 8,003,127, to Liversidge, et al., incorporated by reference herein in its entirety. In a specific embodiment, the corticosteroid is dexamethasone.

In some embodiments, the at least two therapeutic agents and the optional corticosteroid are co-administered simultaneously; in other embodiments, the at least two therapeutic agents and the optional corticosteroid are consecutively or sequentially administered. In another embodiment the at least two therapeutic agents and optional corticosteroid are administered prior to administration of the antibody, as a means of pretreating the subject prior to desensitization via antigen or antibody.

Rapid desensitization with antigen or antibody is a careful process that may take several hours. Because certain therapeutic agents have relatively short half-lives, in some embodiments one or more of the therapeutic agents may be administered more than once during rapid desensitization. Such repeated administration maintains the suppressive effects of the therapeutic agent(s) throughout the rapid desensitization process. In some embodiments, the two or more therapeutic agents are administered at predetermined intervals throughout the rapid desensitization process, for example, once every hour, every 90 minutes, every two hours, etc. until the rapid desensitization is completed. In other embodiments, the subject is monitored for signs and symptoms of anaphylaxis and one or more of the therapeutic agents are administered repeatedly as needed throughout the rapid desensitization process.

Rapid desensitization with antigen or antibody entails administration of escalating doses of antigen or antibody to a subject. During the process, after the initial dose of two or more therapeutic agents and as the dose of antigen or antibody is escalated, the subject may benefit from repeated administration of the two or more therapeutic agents prior to a subsequent dose of antigen or antibody. Such repeated administration(s) of the two or more therapeutic agents serve to maintain the suppressive effects of the therapeutic agent (s) throughout the desensitization process. In some embodiments, the two or more therapeutic agents are administered prior to each dose of antigen or antibody. In other embodiments, the subject is monitored for signs and symptoms of anaphylaxis and the two or more therapeutic agents are administered repeatedly as needed throughout the rapid desensitization process.

In another embodiment, a method of suppressing IgE-mediated anaphylaxis associated with immunotherapeutic desensitization of a subject in need thereof is provided, the method comprising: a) pretreating the subject with a combination of at least two therapeutic agents selected from the group consisting of an antihistamine, one or more beta-adrenergic agonists, and one or more tyrosine kinase antagonists; and b) administering to the subject an antibody selected from the group consisting of an anti-IgE monoclonal antibody, an anti-Fc epsilon receptor I alpha (FcεRIα) monoclonal antibody, and combinations thereof, wherein the pretreating step (a) suppresses IgE-mediated anaphylaxis in the subject. In some embodiments, the method comprises administering an antihistamine in combination with one or more beta-adrenergic agonists, or an antihistamine in combination with one or more tyrosine kinase antagonists. In other embodiments, the methods comprise administration of two or more beta-adrenergic agonists in combination, or two or more tyrosine kinase antagonists in combination. In still other embodiments, the methods comprise administration of a combination of an antihistamine, at least one beta-adrenergic agonist, and at least one tyrosine kinase antagonist. In another embodiment, the method comprises administering at least two therapeutic agents selected from the group consisting of triprolidine, doxepin, indacaterol, terbutaline, albuterol, imatinib, and fostamatinib. In another embodiment, the method comprises administering at least two therapeutic agents selected from the group consisting of triprolidine or doxepin and one or more of indacaterol, terbutaline, albuterol, imatinib, and fostamatinib.

In another embodiment, the method further comprises administering a corticosteroid in addition to the at least two therapeutic agents. In some embodiments, the at least two therapeutic agents and the optional corticosteroid are co-administered simultaneously; in other embodiments, the at least two therapeutic agents and the optional corticosteroid are consecutively or sequentially administered. In another embodiment the at least two therapeutic agents and optional corticosteroid are administered prior to administration of the antibody, as a means of pretreating the subject. In a very specific embodiment, the corticosteroid is dexamethasone.

In a specific embodiment, the antihistamine is triprolidine and/or doxepin. In another specific embodiment, the beta-adrenergic agonist is selected from the group consisting of indacaterol, terbutaline, and albuterol. In another specific embodiment, the tyrosine kinase antagonist is selected from the group consisting of imatinib and fostamatinib.

Pharmaceutical Compositions

The compositions of the embodiments disclosed herein comprise a pharmaceutical composition for suppressing IgE-mediated anaphylaxis comprising (a) a safe and effective amount of at least two therapeutic agents selected from the group consisting of triprolidine, doxepin, indacaterol, terbutaline, albuterol, imatinib, and fostamatinib; and (b) one or more pharmaceutically-acceptable excipients. In a more specific embodiment, the composition comprises (a) a safe and effective amount of at least two therapeutic agents selected from the group consisting of triprolidine or doxepin and one or more of indacaterol, terbutaline, albuterol, imatinib, and fostamatinib; and (b) one or more pharmaceutically-acceptable excipients. In certain embodiments, the pharmaceutical compositions further comprise a corticosteroid.

The term "excipient," as used herein, refers to any inactive substance incorporated into a pharmaceutical composition as a carrier for an active pharmaceutical ingredient. In one embodiment, the at least one pharmaceutically acceptable excipient is selected from the group consisting of polymers, resins, plasticizers, fillers, lubricants, diluents, solvents, co-solvents, buffer systems, surfactants, preservatives, sweetening agents, flavoring agents, pharmaceutical grade dyes or pigments, viscosity agents and combinations thereof. Suitable pharmaceutical excipients are well-known in the art. See, for example, *Handbook of Pharmaceutical Excipients, Sixth Edition*, edited by Raymond C. Rowe (2009). Further, the skilled artisan will appreciate that certain excipients may be more desirable or suitable for certain modes of administration of an active ingredient. It is within the purview of the skilled artisan to select the appropriate excipients for a given pharmaceutical composition.

A "safe and effective amount" of a therapeutic agent is an amount that is effective to suppress IgE-mediated anaphylaxis or treat damage IgE-mediated anaphylaxis in a subject, without undue adverse side effects (such as toxicity, irritation, or allergic response), commensurate with a reasonable risk/benefit ratio when used in the manner of this invention. The specific safe and effective amount will vary with such factors as the physical condition of the patient, the duration of treatment, the nature of concurrent therapy, if any, the dosage form used, the excipient(s) employed, and the dosage regimen desired.

The compositions of the invention may be provided in a variety of forms suitable for oral, intravenous, subcutaneous, intramuscular, intraperitoneal, sublingual, rectal, nasal, pulmonary inhalation/nebulization, and transdermal administration. Further, the skilled artisan will appreciate that certain excipients may be more desirable or suitable for certain modes of administration of an active ingredient. It is within the purview of the skilled artisan to select the appropriate excipients for a given pharmaceutical composition and mode of administration.

Examples of suitable oral dosage forms include tablets, lozenges, aqueous or oily suspensions, dispersible powders or granules, emulsions, hard or soft capsules, syrups or elixirs. Compositions intended for oral use may be prepared according to any method known in the art for the manufacture of pharmaceutical compositions and such compositions my may contain one or more excipients. Such compositions may be coated by conventional methods, typically with pH or time-dependent coatings, such that the active ingredient is released in the gastrointestinal tract in the vicinity of the desired application, or at various times to extend the desired action. Suitable coatings include, but are not limited to, one or more of cellulose acetate phthalate, polyvinylacetate phthalate, hydroxypropyl methyl cellulose phthalate, ethyl cellulose, Eudragit® coatings, waxes and shellac.

In certain embodiments, the pharmaceutical composition further comprises a corticosteroid. In specific embodiment, the corticosteroid comprises dexamethasone.

In another embodiment, the pharmaceutical composition further comprises an antibody selected from the group consisting of an anti-IgE monoclonal antibody, an anti-Fc epsilon receptor I alpha (FcεRIα) monoclonal antibody, and combinations thereof.

In a very specific embodiment, the at least two therapeutic agents comprise triprolidine, indacaterol, and fostamatinib.

In another very specific embodiment, the at least two therapeutic agents comprise triprolidine or doxepin and one or more of fostamatinib, indacaterol, imatinib, terbutaline, or albuterol. In another very specific embodiment, the at least two therapeutic agents comprise triprolidine or doxepin and one of fostamatinib, indacaterol, imatinib, terbutaline, or albuterol.

In another very specific embodiment, the at least two therapeutic agents comprise triprolidine, fostamatinib, and imatinib. In another very specific embodiment, the at least two therapeutic agents comprise triprolidine, albuterol, and fostamatinib.

EXAMPLES

The following examples are given by way of illustration and are in no way intended to limit the scope of the present invention.

Example 1

Suppression of Anti-IgE mAb-Induced Anaphylaxis in BALB/c Mice by Triprolidine, Fostamatinib, Imatinib, and Combinations Thereof 4-8 BALB/c female mice, age 8-12 weeks, were used in typical experiments. Anaphylaxis was induced by injecting mice intravenously with 20 µg EM-95 (rat IgG2a anti-mouse IgE mAb). Rectal temperature was monitored for 60 minutes in order to determine the severity of anaphylaxis. Drugs used to inhibit anaphylaxis were injected intravenously or intraperitoneally 30 minutes prior to injection of EM-95. Doses were as follows: 200 µg/mouse antihistamine (AH, triprolidine); 1.25 mg/mouse imatinib; 40 mg/kg fostamatinib.

Figure 1:
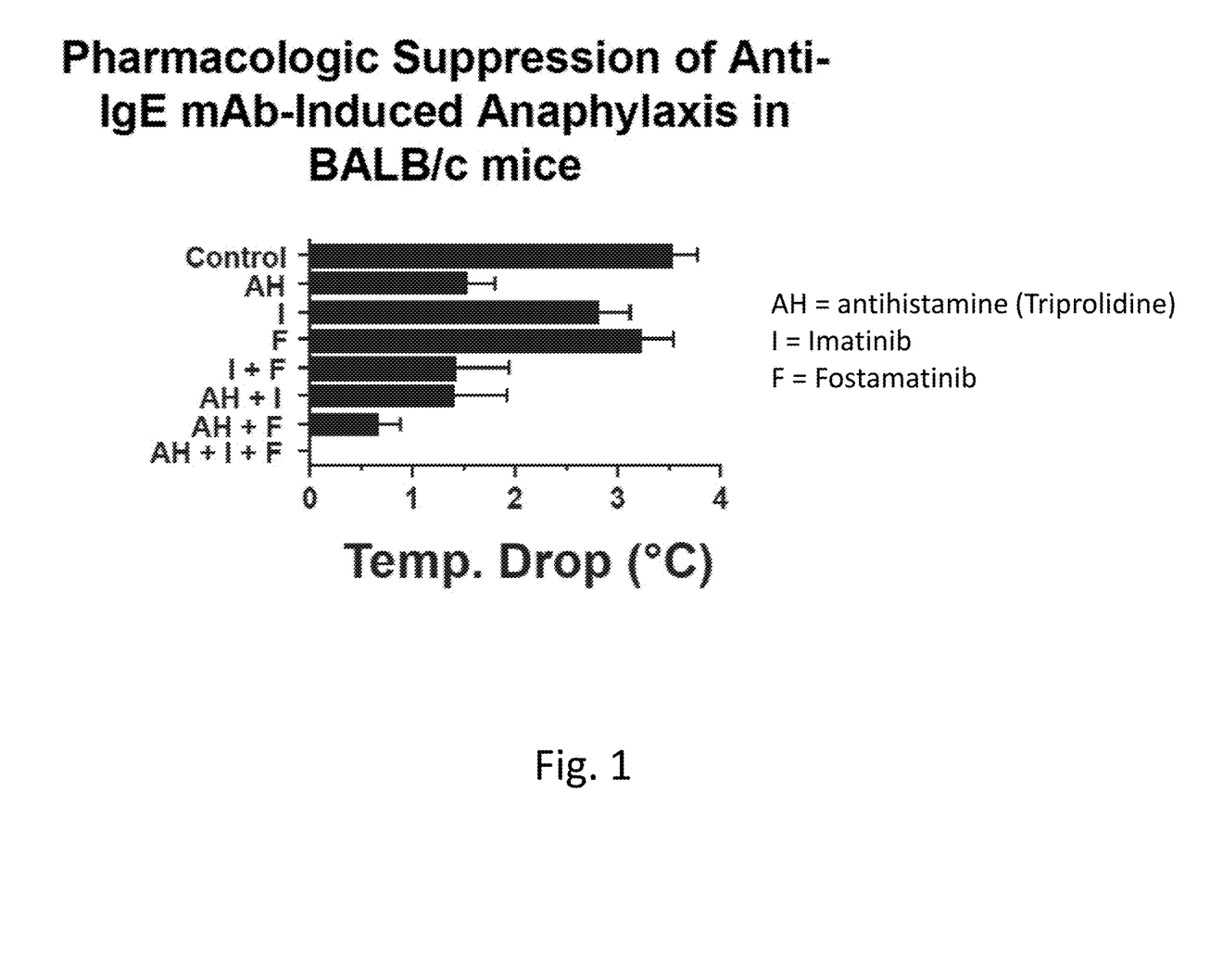
FIG. 1 shows suppression of anti-IgE mAb-induced anaphylaxis in BALB/c mice. Control=vehicle; AH=antihistamine (triprolidine); I=imatinib; F=fostamatinib. Anaphylaxis/suppression is measured as a function of temperature change.

Results are reported in FIG. 1 and show that triprolidine in combination with imatinib and fostamatinib substantially completely suppressed anaphylaxis. Synergistic suppression was observed with the combinations of imatinib+fostamatinib; imatinib+triprolidine; fostamatinib+triprolidine; and fostamatinib+triprolidine+imatinib.

Example 2

Suppression of Anti-IgE mAb-Induced Anaphylaxis in BALB/c Mice by Triprolidine, Fostamatinib, Indacaterol, and Combinations Thereof 4-8 BALB/c female mice, age 8-12 weeks, were used in typical experiments. Anaphylaxis was induced by injecting mice intravenously with 20 µg EM-95 (rat IgG2a anti-mouse IgE mAb). Rectal temperature was monitored for 60 minutes in order to determine the severity of anaphylaxis. Drugs used to inhibit anaphylaxis were injected subcutaneously, intravenously, or intraperitoneally 30 to 60 minutes prior to injection of EM-95. Doses were as follows: 200 µg/mouse triprolidine; 2.5 mg/kg indacaterol; 80 mg/kg fostamatinib. Serum mouse mast cell protease 1 (MMCP1) levels were determined by ELISA three hours after EM-95 injection to determine the extent of mast cell degranulation.

Figure 2:
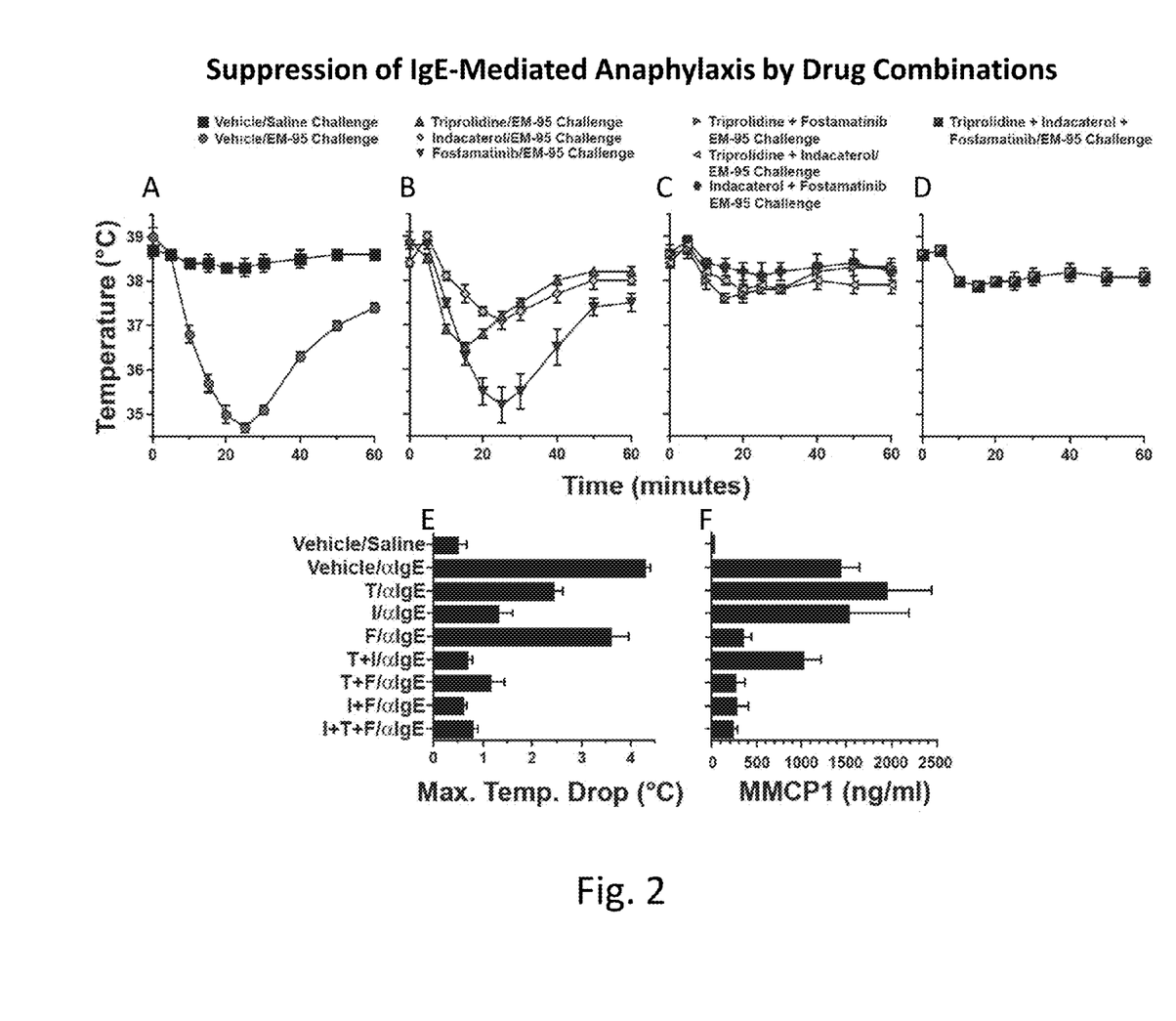
FIG. 2 shows suppression of anti-IgE mAb-induced anaphylaxis in BALB/c mice by different drug combinations as measured by temperature change over time (FIGS. 2A-2D), maximum temperature drop (FIG. 2E), or serum mouse mast cell specific serine protease 1 (MMCP1) (FIG. 2F).

Results are reported in FIG. 2. FIGS. 2A-2E show the combinations of triprolidine+indacaterol, triprolidine+fostamatinib, indacaterol+fostamatinib, and indacaterol+triprolidine+fostamatinib each effectively suppress IgE-mediated anaphylaxis. Further, results indicate that fostamatinib synergizes with indacaterol or triprolidine, alone or in combination, to suppress IgE-mediated anaphylaxis. FIG. 2F shows that fostamatinib effectively suppresses mast cell degranulation in BALB/c mice.

Example 3

Suppression of IgE-Mediated Anaphylaxis by Drug Combinations in IL-4-Sensitized BALB/c Mice 4-8 BALB/c female mice, age 8-12 weeks, were used in typical experiments. Mice were made particularly sensitive to anaphylaxis by treatment with interleukin-4 (IL-4). Anaphylaxis was induced by injecting mice intravenously with 20 µg EM-95 (rat IgG2a anti-mouse IgE mAb). Rectal temperature was monitored for 60 minutes in order to determine the severity of anaphylaxis. Drugs used to inhibit anaphylaxis were injected subcutaneously, intravenously or intraperitoneally 15 to 60 minutes prior to injection of EM-95. Doses were as follows: 200 µg/mouse triprolidine; 2.5 mg/kg indacaterol; 80 mg/kg fostamatinib.

Figure 3:
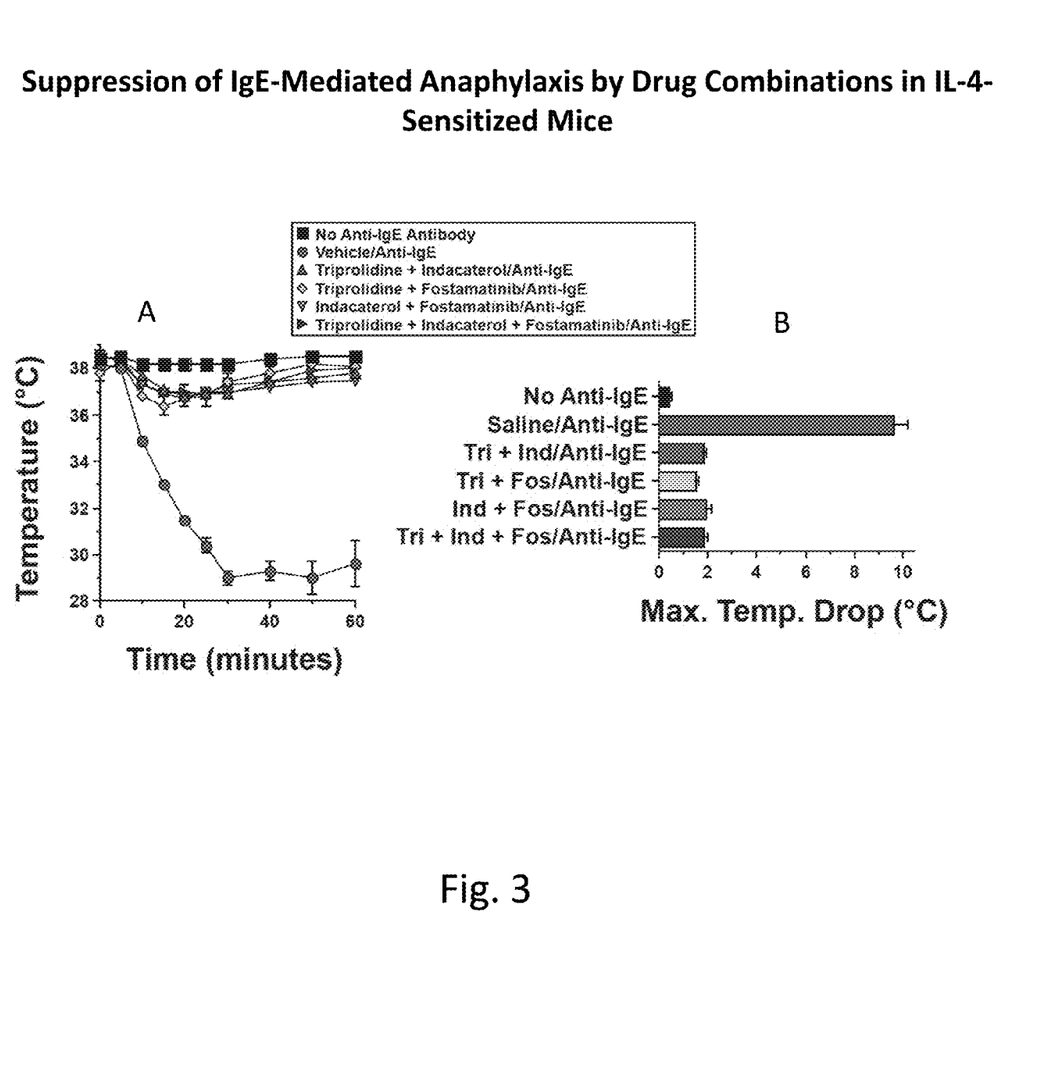
FIG. 3 shows suppression of anti-IgE mAb-induced anaphylaxis by combinations of therapeutic agents in IL-4 sensitized BALB/c mice, as a function of temperature change over time (FIG. 3A) and maximum (max) temperature drop (FIG. 3B). Combinations include triprolidine+indacaterol, triprolidine+fostamatinib, indacaterol+fostamatinib, and triprolidine+indacaterol+fostamatinib, each in combination with anti-IgE mAb challenge.

Results are reported in FIG. 3 and show that each of the tested drug combinations strongly suppresses IgE-mediated anaphylaxis in BALB/c mice.

Example 4

Suppression of IgE-Mediated Anaphylaxis by Terbutaline in BALB/c Mice 4-8 BALB/c female mice, age 8-12 weeks, were used in typical experiments. Anaphylaxis was induced by injecting mice intravenously with 20 µg EM-95 (rat IgG2a anti-mouse IgE mAb). Rectal temperature was monitored for 60 minutes in order to determine the severity of anaphylaxis. Terbutaline was injected subcutaneously 30 minutes prior to injection of EM-95. Doses were as follows: 0.125, 1.5, and 2 mg/kg terbutaline.

Figure 4:
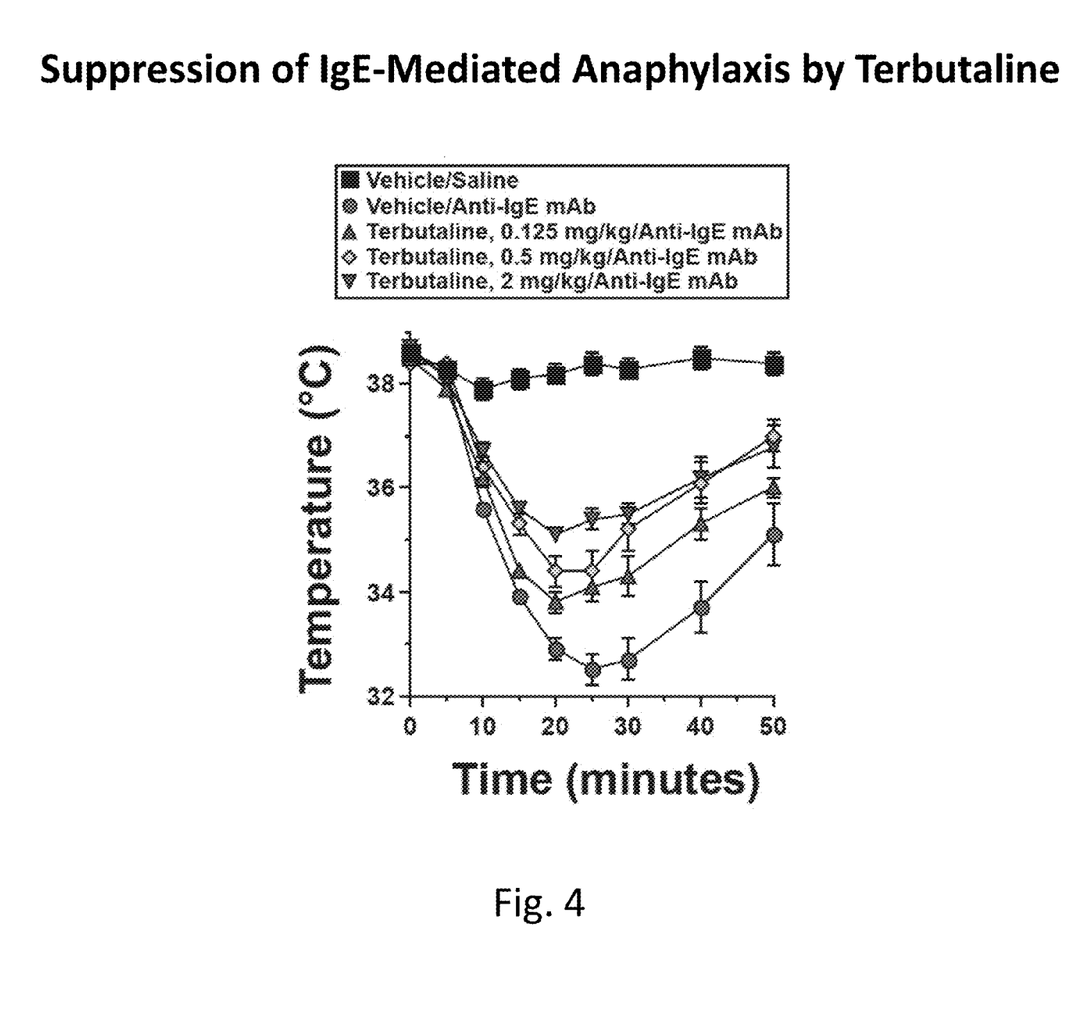
FIG. 4 shows suppression of anti-IgE mAb-induced anaphylaxis in BALB/c mice by terbutaline at various doses (0.125 mg/kg, 0.5 mg/kg, and 2 mg/kg) in combination with anti-IgE mAb challenge, as a function of temperature change over time.

Results are reported in FIG. 4 and show that terbutaline causes dose-dependent suppression of IgE-mediated anaphylaxis in BALB/c mice challenged with EM-95. However, it is noted that even a 16-fold increase in dose of terbutaline does not suppress anaphylaxis to the same degree as a two-drug combination. See, for example, FIG. 5.

Example 5

Suppression of IgE-Mediated Anaphylaxis by Combinations of Terbutaline and Triprolidine in BALB/c Mice 4-8 BALB/c female mice, age 8-12 weeks, were used in typical experiments. Anaphylaxis was induced by injecting mice intravenously with 20 µg EM-95 (rat IgG2a anti-mouse IgE mAb). Rectal temperature was monitored for 60 minutes in order to determine the severity of anaphylaxis. Drugs were injected subcutaneously or intraperitoneally 30 to 60 minutes prior to injection of EM-95. Doses were as follows: 0.5 mg/kg terbutaline; 200 µg/mouse triprolidine; 0.5 mg/kg terbutaline+200 µg/mouse triprolidine.

Figure 5:
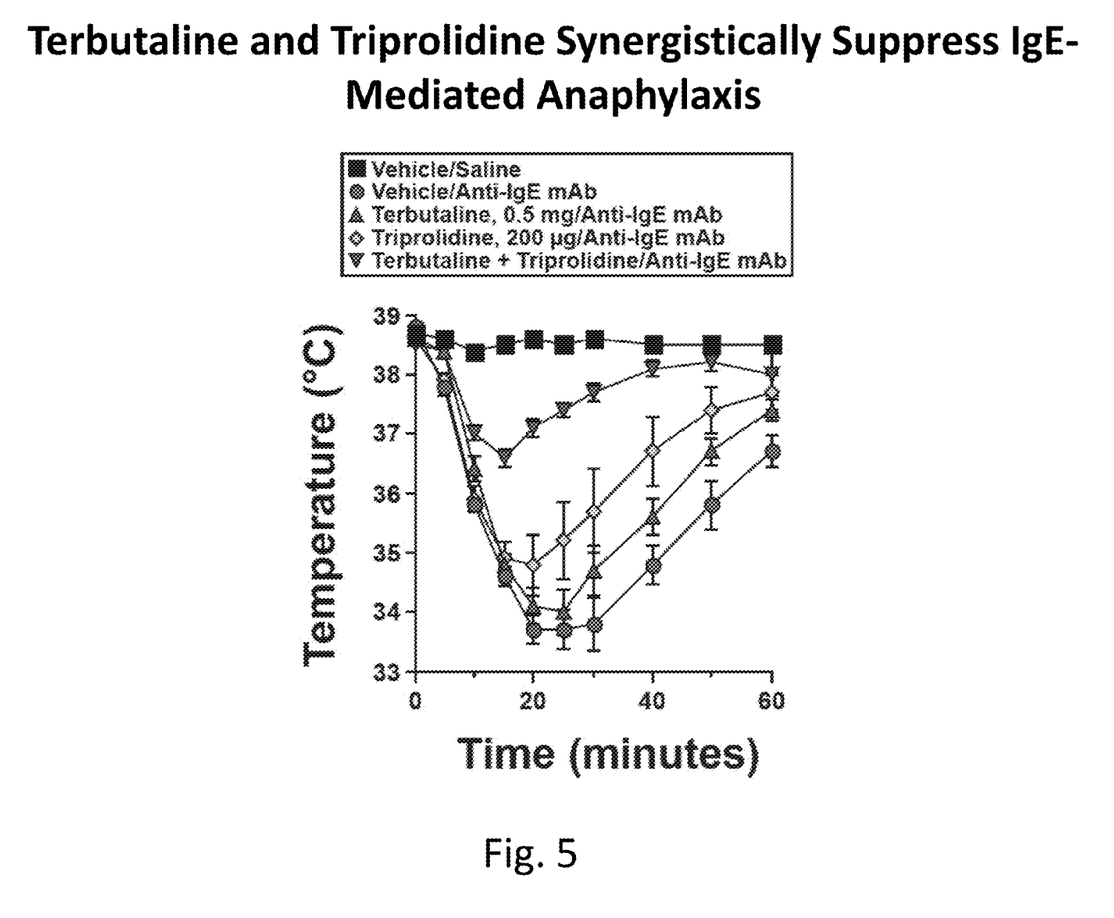
FIG. 5 shows suppression of anti-IgE mAb-induced anaphylaxis of terbutaline, triprolidine, and terbutaline+triprolidine, each in combination with anti-IgE mAb challenge, as a function of temperature change over time.

Results are reported in FIG. 5 and show synergistic suppression of IgE-mediated anaphylaxis by terbutaline+triprolidine in BALB/c mice.

Example 6

Suppression of IgE-Mediated Anaphylaxis by Albuterol in BALB/c Mice 4-8 BALB/c female mice, age 8-12 weeks, were used in typical experiments. Anaphylaxis was induced by injecting mice intravenously with 20 µg EM-95 (rat IgG2a anti-mouse IgE mAb). Rectal temperature was monitored for 60 minutes in order to determine the severity of anaphylaxis. Albuterol was injected intraperitoneally 30 minutes prior to injection of EM-95. Doses were as follows: 5, 10, and 20 mg/kg albuterol.

Figure 6:
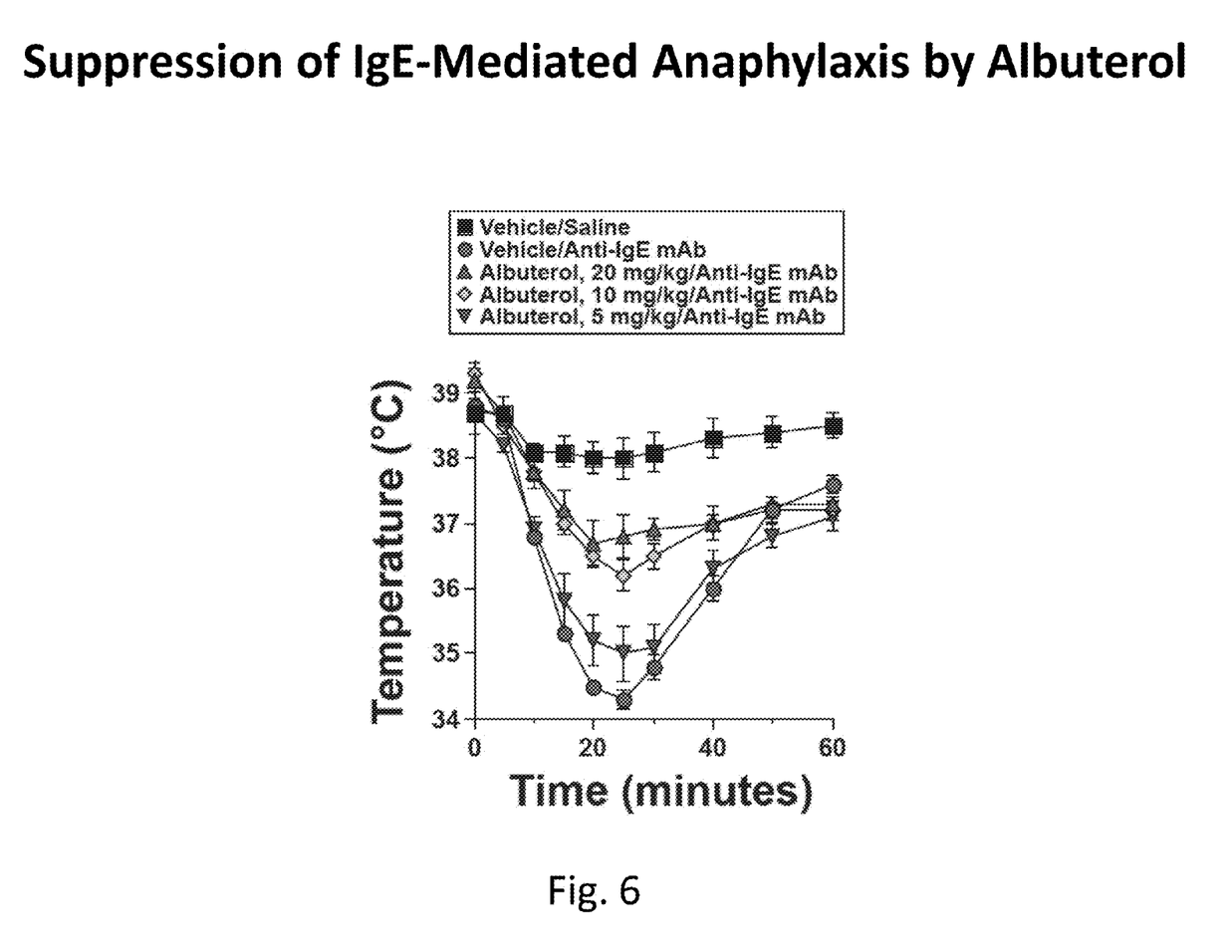
FIG. 6 shows suppression of anti-IgE mAb-induced anaphylaxis in BALB/c mice by albuterol at various doses (5 mg/kg, 10 mg/kg, and 20 mg/kg) in combination with anti-IgE mAb challenge, as a function of temperature change over time.

Results are reported in FIG. 6 and show that albuterol causes dose-dependent suppression of anaphylaxis in anti-IgE mAb challenged BABL/c mice. However, it is noted that even a 4-fold increase in dose does not suppress anaphylaxis to the same degree as a two-drug combination. See, for example, FIG. 7.

Example 7

Suppression of IgE-Mediated Anaphylaxis by Combinations of Albuterol and Triprolidine in BALB/c Mice 4-8 BALB/c female mice, age 8-12 weeks, were used in typical experiments. Anaphylaxis was induced by injecting mice intravenously with 20 µg EM-95 (rat IgG2a anti-mouse IgE mAb). Rectal temperature was monitored for 60 minutes in order to determine the severity of anaphylaxis. Drugs were injected intraperitoneally 30 minutes prior to injection of EM-95. Doses were as follows: 5 mg/kg albuterol; 200 µg/mouse triprolidine; 5 mg/kg albuterol+200 µg/mouse triprolidine.

Figure 7:
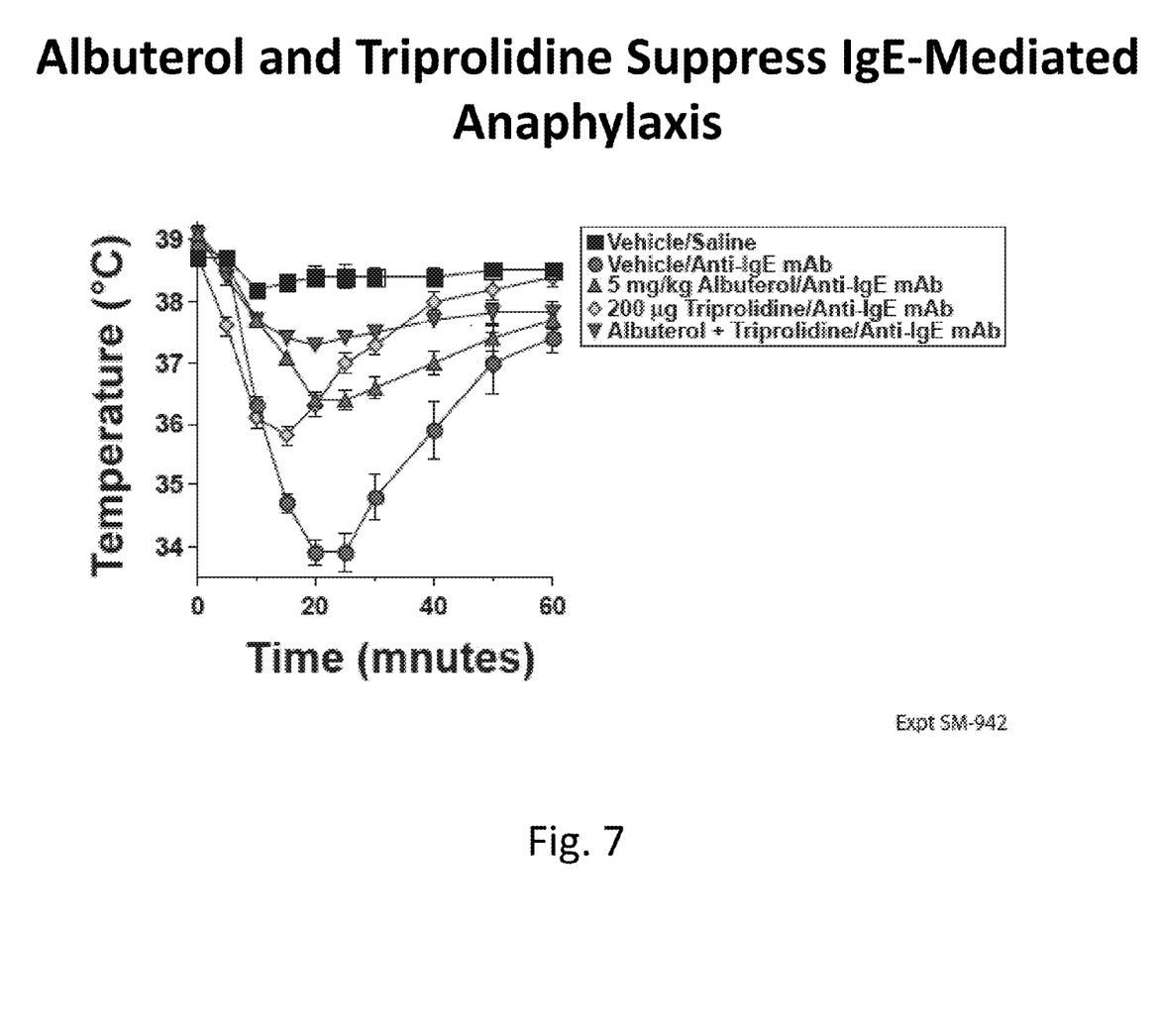
FIG. 7 shows suppression of anti-IgE mAb-induced anaphylaxis in BALB/c mice by albuterol, triprolidine, and albuterol+triprolidine, each in combination with anti-IgE mAb challenge, as a function of temperature change over time.

Results are reported in FIG. 7 and show that the combination of albuterol+triprolidine strongly suppresses anti-IgE mAb induced anaphylaxis in BALB/c mice.

Example 8

Suppression of IgE-Mediated Anaphylaxis by Combinations of Albuterol, Triprolidine, and Fostamatinib in BALB/c Mice 4-8 BALB/c female mice, age 8-12 weeks, were used in typical experiments. Anaphylaxis was induced by injecting mice intravenously with 20 µg EM-95 (rat IgG2a anti-mouse IgE mAb). Rectal temperature was monitored for 60 minutes in order to determine the severity of anaphylaxis. Drugs were injected intraperitoneally 60 minutes prior to injection of EM-95. Doses were as follows: 2.5 mg/kg albuterol; 200 µg/mouse triprolidine; 40 mg/kg fostamatinib; 2.5 mg/kg albuterol+200 µg/mouse triprolidine+40 mg/kg fostamatinib.

Figure 8:
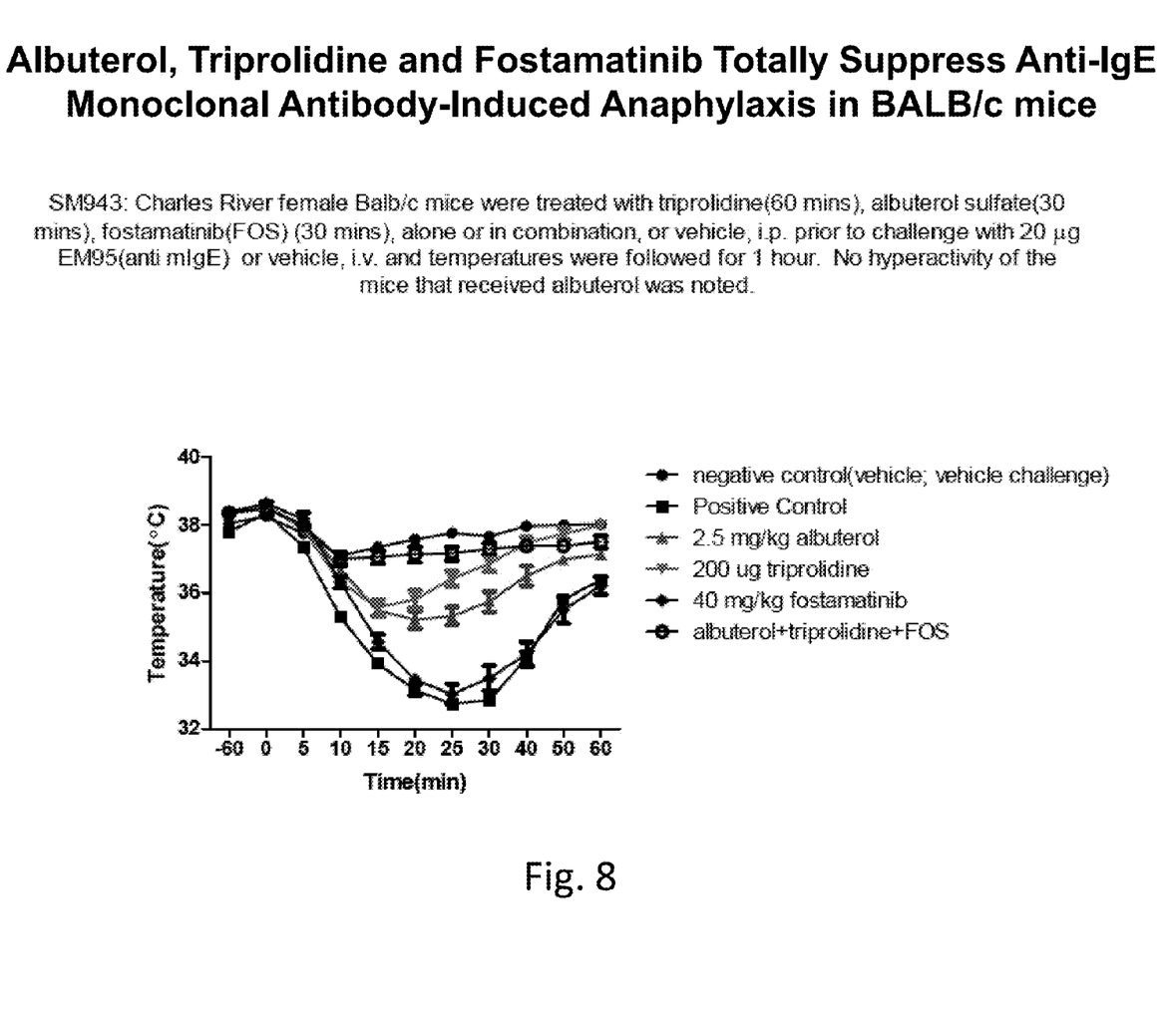
FIG. 8 shows suppression of anti-IgE mAb-induced anaphylaxis in BALB/c mice by albuterol, triprolidine, fostamatinib, and a combination of the same, as a function of temperature change over time.

Results are reported in FIG. 8 and show that the combination of albuterol, triprolidine, and fostamatinib completely suppresses anti-IgE mAb-induced anaphylaxis in BALB/c mice. While not desiring to be bound by theory, it is believed that fostamatinib synergizes with triprolidine and albuterol.

Example 9

Equal Suppression of IgE-Mediated Anaphylaxis by Triprolidine and Doxepin in BALB/c Mice 4-8 BALB/c female mice, age 8-12 weeks, were used in typical experiments. Anaphylaxis was induced by injecting mice intravenously with 20 µg EM-95 (rat IgG2a anti-mouse IgE mAb). Rectal temperature was monitored for 60 minutes in order to determine the severity of anaphylaxis. Drugs were injected intraperitoneally prior to injection of EM-95. Doses were as follows: doxepin, 10 mg/kg, injected i.p. 5 minutes prior to EM-95 injection; triprolidine, 200 µg/mouse, injected i.p. 1 hour prior to injection of EM-95.

Figure 9:
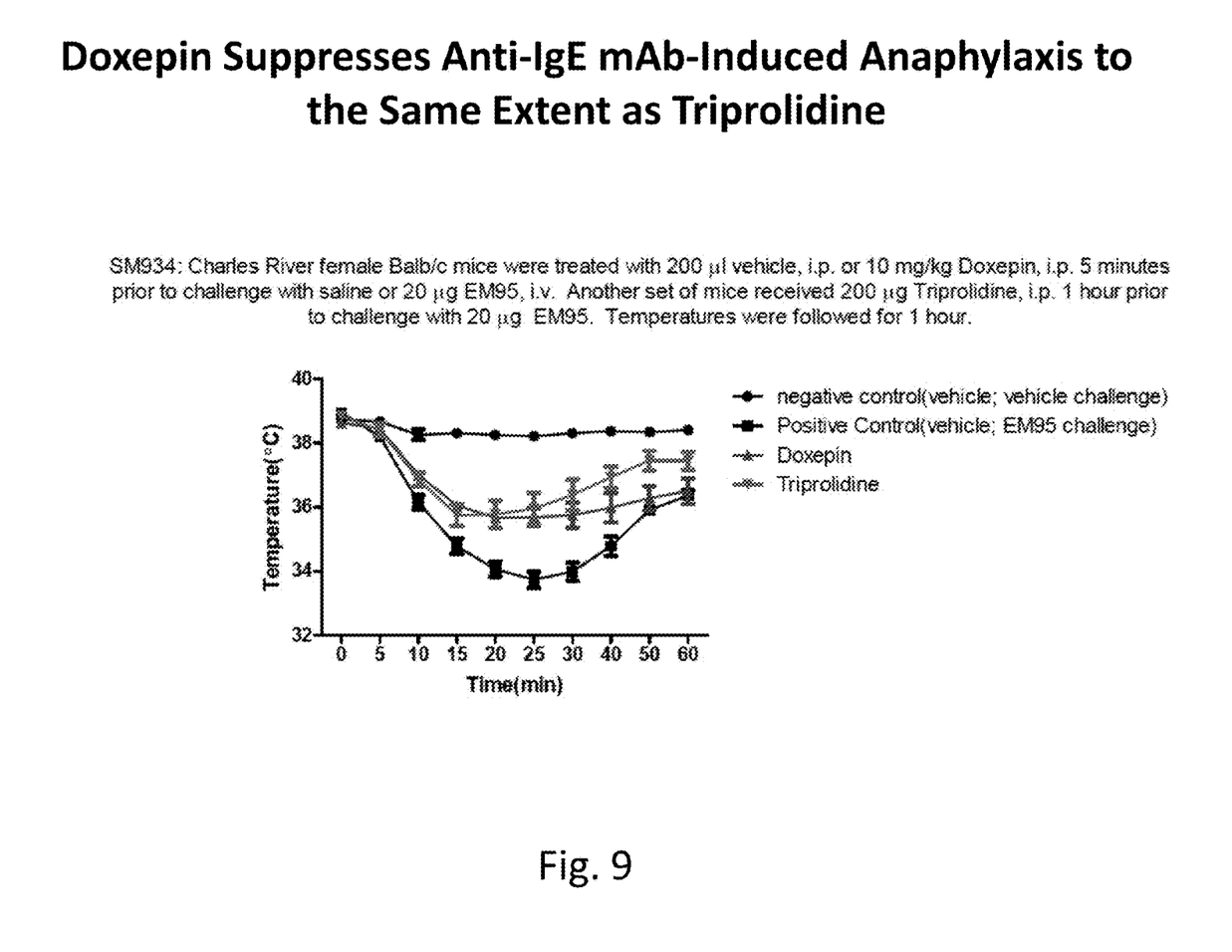
FIG. 9 shows equal suppression of anti-IgE mAB-induced anaphylaxis in BALB/c mice by triprolidine and by the highly potent dual H1/H2 receptor antagonist doxepin.

Results are reported in FIG. 9 and show that doxepin and triprolidine suppress IgE-mediated anaphylaxis to the same extent, even though doxepin is more potent that triprolidine and, unlike triprolidine, suppresses the H2 histamine receptor in addition to the H1 histamine receptor that is selectively suppressed by triprolidine.

Example 10

Complete Suppression of Anti-Human FcεRIα mAb-Induced Anaphylaxis in Mice that Express Human FcεRIα Instead of Mouse FcεRIα

4-8 BALB/c background transgenic mice that express human FcεRIα instead of mouse FcεRIα, age 8-12 weeks, were used in typical experiments. Anaphylaxis was induced by injecting mice intravenously with 50 µg of AER-37 mouse IgG anti-human FcεRIα mAb. Rectal temperature was monitored for 60 minutes in order to determine the severity of anaphylaxis. Drugs were injected prior to injection of AER-37 or control. Doses were as follows: triprolidine, 200 µg/mouse i.p. 60 minutes prior to AER-37 or control injection; indacaterol, 2.5 mg/kg s.c 60 minutes prior to AER-37 or control injection; and fostamatinib, 40 mg/kg i.p. 30 minutes prior to AER-37 or control injection.

Figure 10:
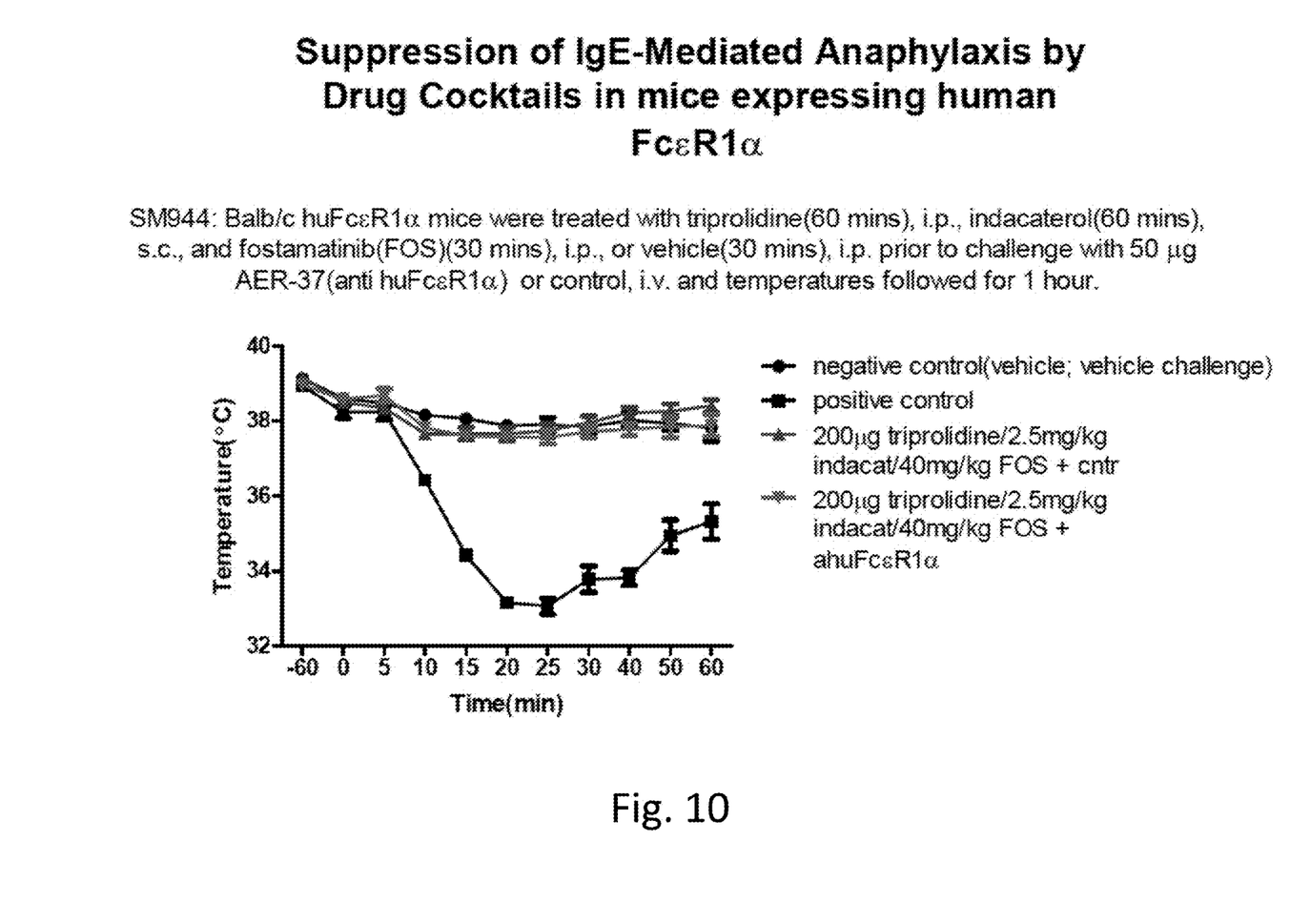
FIG. 10 shows complete suppression of anti-human FcεRIα mAb-induced anaphylaxis in BALB/c background mice that express human FcεRIα instead of mouse FcεRIα by a combination of triprolidine, fostamatinib, and indacaterol.

Results are reported in FIG. 10 and show that the combination of triprolidine, indacaterol, and fostamatinib completely suppresses anaphylaxis that would otherwise be induced by anti-human FcεRIα mAb in mice that express human rather than mouse FcεRIα.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

We claim:

1. A method of suppressing IgE-mediated anaphylaxis comprising administering to a subject in need thereof a combination of an antihistamine, one or more beta-adrenergic agonists, and one or more tyrosine kinase antagonists, wherein the antihistamine is triprolidine, the one or more beta-adrenergic agonists comprises albuterol, and the one or more tyrosine kinase antagonists comprises fostamatinib.

2. The method of claim 1, further comprising administering an antibody selected from the group consisting of an anti-IgE monoclonal antibody, an anti-Fc epsilon receptor I alpha (FcεRIα) monoclonal antibody, and combinations thereof.

3. The method of claim 2, wherein the one or more beta-adrenergic agonists further comprises a beta-adrenergic agonist selected from the group consisting of indacaterol, terbutaline, and combinations thereof.

4. The method of claim 2, wherein the one or more tyrosine kinase antagonists further comprises imatinib.

5. The method of claim 2, further comprising administering a corticosteroid.

6. The method of claim 5, wherein the corticosteroid comprises dexamethasone.

7. The method of claim 2, wherein the combination of the antihistamine, the one or more beta-adrenergic agonists, and the one or more tyrosine kinase antagonists is administered prior to administering the antibody.

8. The method of claim 1, wherein the antihistamine, the one or more beta-adrenergic agonists, and the one or more tyrosine kinase antagonists are administered simultaneously or consecutively.

9. The method of claim 1, wherein the combination consists essentially of triprolidine, albuterol, and fostamatinib.

10. A method of suppressing IgE-mediated anaphylaxis associated with immunotherapeutic desensitization of a subject in need thereof, the method comprising:
  a) administering to the subject a combination of an antihistamine, one or more beta-adrenergic agonists, and one or more tyrosine kinase antagonists, wherein the antihistamine is triprolidine, the one or more beta-adrenergic agonists comprises albuterol, and the one or more tyrosine kinase antagonists comprises fostamatinib; and
  b) administering to the subject an antibody selected from the group consisting of an anti-IgE monoclonal antibody, an anti-Fc epsilon receptor I alpha (FcεRIα) monoclonal antibody, and combinations thereof,
  wherein the administering step (a) suppresses IgE-mediated anaphylaxis in the subject.

11. The method of claim 10, further comprising administering a corticosteroid.

12. The method of claim 11, wherein the corticosteroid comprises dexamethasone.

13. The method of claim 11, wherein the corticosteroid is administered prior to administering the antibody.

14. The method of claim 10, wherein the one or more beta-adrenergic agonists further comprises a beta-adrenergic agonist selected from the group consisting of indacaterol, terbutaline, and combinations thereof.

15. The method of claim 10, wherein the one or more tyrosine kinase antagonists further comprises imatinib.

* * * * *

UNITED STATES PATENT AND TRADEMARK OFFICE
CERTIFICATE OF CORRECTION

PATENT NO. : 9,795,618 B2  
APPLICATION NO. : 14/633305  
DATED : October 24, 2017  
INVENTOR(S) : Fred D. Finkelman, Marat V. Khodoun and Suzanne C. Morris Page 1 of 1

It is certified that error appears in the above-identified patent and that said Letters Patent is hereby corrected as shown below:

In the Specification

On Column 1, after the heading, FEDERALLY SPONSORED RESEARCH OR DEVELOPMENT, please replace the paragraph with the following paragraph:

This invention was made with government support under 1R01AI113162 awarded by National Institutes of Health. The government has certain rights in the invention.

Signed and Sealed this  
Seventh Day of January, 2020

Andrei Iancu  
*Director of the United States Patent and Trademark Office*